United States Patent [19]

Englert et al.

[11] Patent Number: 5,364,878
[45] Date of Patent: Nov. 15, 1994

[54] USE OF SUBSTITUTED 3,4-DIHYDRO-2H-BENZOPYRANS AS REMEDIES FOR OBSTRUCTIVE FUNCTIONAL DISORDERS OF THE LUNGS

[75] Inventors: Heinrich C. Englert, Hofheim am Taunus; Erik Klaus; Dieter Mania, both of Kelkheim; Bernward Schölkens, Kelkheim, all of Germany

[73] Assignee: Hoechst Aktiengesellschaft, Frankfurt am Main, Germany

[21] Appl. No.: 4,648

[22] Filed: Jan. 14, 1993

Related U.S. Application Data

[63] Continuation of Ser. No. 764,966, Sep. 25, 1991, abandoned, which is a continuation of Ser. No. 630,436, Dec. 20, 1990, abandoned, which is a continuation of Ser. No. 380,309, Jul. 17, 1989, abandoned.

[30] Foreign Application Priority Data

Jul. 19, 1988 [DE] Germany ............................ 3824446

[51] Int. Cl.$^5$ ..................... A61K 31/55; A61K 31/44; A61K 31/40
[52] U.S. Cl. .................... 514/422; 514/212; 514/337; 514/826
[58] Field of Search ................. 514/422, 212, 337, 826

[56] References Cited

U.S. PATENT DOCUMENTS

| | | | |
|---|---|---|---|
| 4,687,779 | 8/1987 | Evans | 514/456 |
| 4,738,963 | 4/1988 | Hamilton et al. | 514/254 |
| 4,772,603 | 9/1988 | Evans | 514/241 |
| 4,782,083 | 11/1988 | Cassidy et al. | 514/241 |
| 4,786,639 | 11/1988 | Evans | 514/254 |
| 4,943,582 | 7/1990 | Evans et al. | 514/320 |
| 4,999,371 | 3/1991 | Englert et al. | 514/422 |
| 5,032,596 | 7/1991 | Williams | 514/302 |

FOREIGN PATENT DOCUMENTS

| | | | |
|---|---|---|---|
| 0176689 | 9/1986 | European Pat. Off. | A61K 31/35 |
| 0207614 | 7/1987 | European Pat. Off. | A61K 31/35 |

OTHER PUBLICATIONS

Ashwood et al., 1986, Synthesis & Antihypertensive Activity of 4-(Cyclic amido)-2H-1-benzopyrans, *J. Med. Chem.* 29:2194–2201.

Englert, et al., "Airway Pharmacology of the Potassium Channel Opener, HOE 234, in Guinea Pigs: in Vitro and in Vivo Studies," European Journal of Pharmacology, vol. 210, pp. 69–75 (1992).

Primary Examiner—Marianne M. Cintins
Assistant Examiner—Kimberly R. Jordan
Attorney, Agent, or Firm—Finnegan, Henderson, Farabow, Garrett & Dunner

[57] ABSTRACT

The use of substituted 3,4-dihydro-2H-benzopyrans as remedies for obstructive functional disorders of the lungs and/or disorders of the efferent urinary passages The use of 3,4-dihydro-2H-benzo[b]pyrans of the formula I

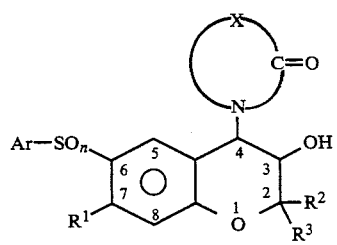

in which
  $R^1$ represents H, OH, $(C_1-C_2)$-alkoxy, $(C_1-C_2)$-alkyl or $NR^4R^5$, where $R^4$ and $R^5$ are identical or different and represent H, $(C_1-C_2)$-alkyl or $(C_1-C_3)$-alkyl-carbonyl,
  $R^2$ and $R^3$ are identical or different and represent alkyl having 1-4 carbon atoms,
  Ar represents an aromatic or heteroaromatic system which is unsubstituted or substituted by 1 to 3 identical or different radicals $(C_1-C_2)$-alkyl, $(C_1-C_2)$-alkoxy, halogen, trifluoromethyl, CN, $NO_2$, CO—$(C_1-C_2)$-alkyl or $SO_m$—$(C_1-C_2)$-alkyl with m=1 or 2,
  n represents 1 or 2,
  X represents a chain $(CH_2)_r$ which can be interrupted by a heteroatom O, S or $NR^6$, where $R^6$ denotes H or $(C_1-C_4)$-alkyl, and r represents the numbers 2, 3, 4 or 5, for the preparation of a remedy for obstructive functional disorders of the lungs and/or disorders of the efferent urinary passages, is described.

7 Claims, No Drawings

USE OF SUBSTITUTED 3,4-DIHYDRO-2H-BENZOPYRANS AS REMEDIES FOR OBSTRUCTIVE FUNCTIONAL DISORDERS OF THE LUNGS

This application is a continuation of application Ser. No. 07/764,966, filed Sep. 25, 1991, now abandoned, which is a continuation of application Ser. No. 07/630,436 filed Dec. 20, 1990, now abandoned, which is a continuation of application Ser. No. 07/380,309, filed Jul. 17, 1989, now abandoned.

DESCRIPTION

The use of substituted 3,4-dihydro-2H-benzopyrans as remedies for obstructive functional disorders of the lungs and/or disorders of the efferent urinary passages.

The invention relates to the use of 3,4-dihydro-2H-benzo[b]pyrans of the formula I

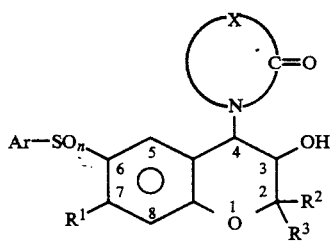

in which
- $R^2$ represents H, OH, $(C_1-C_2)$-alkoxy, $(C_1-C_2)$-alkyl or $NR^4R^5$, where $R^5$ and R are identical or different and represent H, $(C_1-C_2)$-alkyl or $(C_1-C_3)$-alkylcarbonyl,
- $R^2$ and $R^3$ are identical or different and represent alkyl having 1-4 carbon atoms,
- Ar represents an aromatic or heteroaromatic system which is unsubstituted or substituted by 1 to 3 identical or different radicals $(C_1-C_2)$-alkyl, $(C_1-C_2)$-alkoxy, halogen, trifluoromethyl, CN, $NO_2$, CO—$(C_1-C_2)$-alkyl or $SO_m$—$(C_1-C_2)$-alkyl with m=1 or 2,
- n represents 1 or 2,
- X represents a chain $(CH_2)_r$ which can be interrupted by a heteroatom O, S or $NR^6$, where $R^6$ denotes H or $(C_1-C_4)$-alkyl, and r represents the numbers 2, 3, 4 or 5, for the preparation of a remedy for obstructive functional disorders of the lungs and/or disorders of the efferent urinary passages.

An aromatic system Ar is preferably to be understood to be phenyl, naphthyl or biphenylyl, and a 5- or 6-membered heteroaromatic system Ar is preferably a radical of a 5-or 6-membered O, N and/or S heterocyclic ring, especially furyl, thienyl, isothiazolyl, oxazolyl, isoxazolyl, pyrazolyl, imidazolyl, thiazolyl, pyridyl, pyrazinyl, pyrimidinyl, pyridazinyl or triazinyl.

Halogen is to be understood to be F, Cl, Br or I, preferably F and Cl.

Carbon atoms 3 and 4 of the 3,4-dihydro-2H-benzo[b]pyran system (also called "chroman system" hereinafter for brevity) of the formula I are asymmetrically substituted. In this connection, the invention relates only to those compounds which have opposite configurations at these centers, that is to say have a "trans" orientation of the substituents on these carbon atoms. If one of the substituents $R^1ArSO_n$, $R^2$ and/or $R^3$ contains centers of asymmetry, or if $R^2$ and $R^3$ are not the same (and thus generate an asymmetric carbon atom), the invention relates to compounds with centers both of the S and of the R configuration.

The compounds can be in the form of optical isomers, diastereoisomers, astereoisomers, racemates or mixtures thereof.

Preferably used are compounds of the formula I in which $R^1$ to $R^3$ and $ArSO_n$ have the abovementioned meanings, but X represents a chain $(CH_2)_r$ with r=3 or 4.

Very particularly preferably used are those compounds which $R^1$ to $R^3$ have the abovementioned meanings, Ar represents phenyl which is unsubstituted or substituted as defined above, n represents 2, and X represents a chain $(CH_2)_r$ with r=3 or 4.

Especially preferably used are those compounds in which $R^1$ denotes H, $R^2$ and $R^3$ represent $(C_1-C_2)$-alkyl, Ar represents phenyl which is unsubstituted or substituted once by $(C_1-C_2)$-alkyl, $(C_1-C_2)$-alkoxy or halogen, n represents 2, and X represents a chain $(CH_2)_r$ with r=3 or 4.

Likewise preferred are compounds with $R^1$ equal to H, $R^2$ and $R^3$ equal to $(C_1-C_2)$-alkyl, X equal to $(CH_2)_3$, Ar equal to $C_6H_4Cl$, and n equal to 2, as well as those with $R^1$ equal to H, $R^2$ and $R^3$ equal to $(C_1-C_2)$-alkyl, Ar equal to phenyl, n equal to 2, and X equal to $(CH_2)_3$.

EP 0,176,689 describes the use of benzopyrans for respiratory tract diseases and/or disorders of the gastrointestinal tract and/or of the uterus, with special emphasis being placed on those disorders occurring in smooth muscular contractions. EP 207,614 describes the use of benzopyrans for incontinence. Furthermore, J. Med. Chem. 1986, 29, 2194–2201 discloses that compounds of this type may have hypotensive properties. It has now been found, surprisingly, in pharmacological investigations that compounds I are likewise suitable for use as remedies for respiratory tract diseases and/or disorders of the efferent urinary passages.

Hence the invention relates to the use of the compounds of the formula I for the treatment and prophylaxis of the diseases detailed above; particularly preferred in this connection are those diseases in which there is a disturbance of the smooth muscular contractions of the particular organs, such as, for example, asthma, incontinence or renal colic. Particularly important in this connection are those compounds I whose hypotensive properties are less pronounced.

The invention is furthermore directed at a pharmaceutical product for the treatment of obstructive functional disorders of the lungs, which contains a compound I as active substance besides customary additives, as well as at a compound I for use for the treatment of obstructive functional disorders of the lungs and/or of the efferent urinary passages.

Very particularly preferred is the use of 3,4-dihydro-2,2-dimethyl-6- (2-chlorophenylsulfonyl)-trans-4-(2-oxo-1-pyrrolidinyl)-2H-benzo[b]pyran-3-ol for the preparation of a remedy for disorders of the efferent urinary passages and the use of 3,4-dihydro-2,2-dimethyl-6-phenyl-sulfonyl-trans-4-(2-oxo-1-pyrrolidinyl)-2H-benzo[b]pyran-3-ol for the preparation of a remedy for obstructive respiratory tract diseases.

The invention furthermore embraces the use of the compounds according to the invention for the preparation of pharmaceuticals which are used for the treatment and prophylaxis of the abovementioned diseases.

The compounds I can be prepared by the following processes: by a) reacting compounds of the formula II

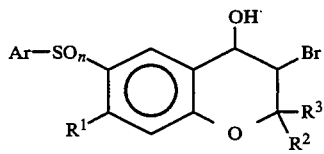

in which $R^1$ to $R^3$ and $ArSO_n$ are as defined above, with lactams of the formula III

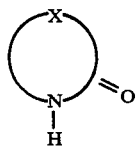

b) reacting compounds of the formula IV

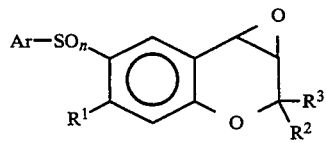

in which $R^1$ to $R^3$ and $ArSO_n$ are as defined above, with the lactams of the formula III, c) acylating compounds of the formula V

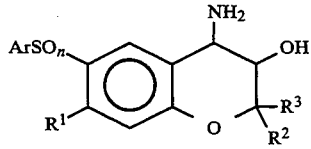

in which $R^1$ to $R^3$ and $ArSO_n$ are as defined above, to give the compounds VI

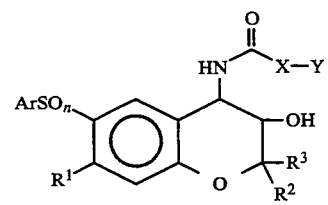

in which Y is a leaving group such as, for example, chlorine or bromine, and $R^1$ to $R^3$ and $ArSO_n$ are as defined above, and cyclizing the latter to give the compounds I, d) oxidizing compounds of the formula VII

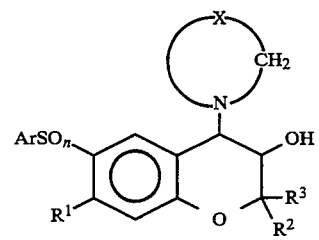

in which $R^1$ to $R^2$ and $ArSO_n$ are as defined above, to give the compounds I.

Where the compounds I are prepared by methods a) or b), this is carried out by reacting the compounds II or IV in a suitable solvent, preferably in dipolar aprotic solvents such as, for example, dimethyl sulfoxide or THF, with the lactams III, preferably with the action of bases such as, for example, sodium hydride, potassium tert.-butylate or similar bases known to be suitable for lactam N-alkylations. The temperature for this reaction can be varied within wide limits; it is preferably carried out between 0° and room temperature or at temperatures which may be slightly above room temperature.

Lactams of the formula III are known in many cases, or they can readily be prepared by methods known from the literature. Compounds II or IV are new. They can be prepared, for example, by the following synthetic route:

Compounds of the formula VIII

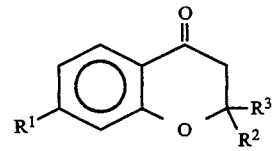

in which $R^1$, $R^2$ and $R^3$ are as defined above, are reacted with acid chlorides $Ar-SO_n-Cl$ in a type of Friedel-Crafts acylation in a manner known per se to give compounds of the formula IX

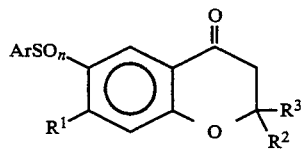

in which $R^1$, $R^2$, $R^3$ and Ar and n are as defined above. The latter are converted by reductions under standard conditions, for example by $NaBH_4$ in methanol, into the compounds X

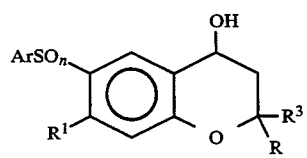

which are then subjected to elimination of water, for example by pyridine/phosphorus oxychloride, resulting in compounds of the formula XI:

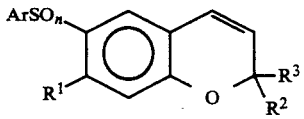

Compounds XI can now easily be converted by standard methods into the epoxides IV or the bromohydrins II.

If in this reaction sequence R means $NH_2$ or OH, protective groups may be necessary, such as, for example, the dimethylaminomethylene group for $NH_2$ or the acetyl or methyl group for the OH group. These are eliminated again at suitable stages, preferably after the reactions described in process a) or b) have been carried out, by conventional methods.

Chromenes of the formula XI are, in some cases, prepared in a manner known per se by thermally induced cyclization of the corresponding propargyl ethers XII

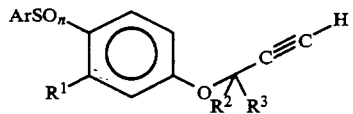

These in turn can be prepared in a manner known per se from the phenols XIII and the propargyl chlorides XIV.

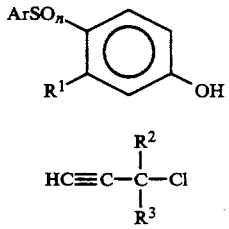

It is possible and particularly beneficial to use processes c) and d) when the final products I are desired as pure enantiomers. Compounds V and VII are, in contrast to compounds I, basic and thus able to form salts with organic acids. It is possible, by crystallization with a suitable optically pure acid such as, for example, (+)-mandelic acid or (+)-lactic acid, in a manner known per se to obtain them as pure enantiomers, and convert them by processes c) and d) into final products I as pure enantiomers.

However, final products I can also be obtained as pure enantiomers from racemic final products I by conventional methods of racemate resolution such as, for example, chromatographic separation using chiral phases, or derivatization of the racemic products with optically pure acid derivatives (ester formation via the 3-hydroxy group of the chroman system) or with optically pure isocyanates (carbamate formation via the 3-hydroxy group). The diastereoisomeric isocyanates or esters obtained in this way can be separated by conventional methods (crystallization or chromatography) and converted into the optically pure final compounds I with elimination of the optically active auxiliary group on the 3-OH group. Separation of the diastereomeric 3-menthoxyacetates has proven particularly advantageous in this connection.

As already mentioned, the compounds I can be used according to the invention as agents for the treatment of obstructive respiratory tract diseases and/or for the treatment of disorders of the efferent urinary passages.

In this connection, pharmaceuticals which contain the compounds I can be administered orally, parenterally, intravenously, rectally or by inhalation, with the preferred administration form being dependent on the disease which is to be treated. In this connection, the compounds I can be used alone or together with pharmaceutical auxiliaries, specifically both in veterinary and in human medicine.

The expert is familiar, on the basis of his expert knowledge, with the auxiliaries which are suitable for the desired pharmaceutical formulation. Besides solvents, gel-formers, suppository bases, tablet auxiliaries and other active substance vehicles, it is possible to use, for example, antioxidants, dispersants, emulsifiers, antifoam agents, flavorings, preservatives, solubilizers or pigments.

For a form for oral use, the active compounds are mixed with the additives suitable for this purpose, such as excipients, stabilizers or inert diluents, and converted by the customary methods into suitable administration forms such as tablets, coated tablets, hard gelatin capsules, aqueous, alcoholic or oily suspensions or aqueous, alcoholic or oily solutions. Examples of inert vehicles which can be used are gum arabic, magnesia, magnesia carbonate, potassium phosphate, lactose, glucose or starch, especially corn starch. This preparation can be carried out both as dry and as wet granules. Examples of suitable oily excipients or solvents are vegetable or animal oils, such as sunflower oil or fish liver oil.

For subcutaneous or intravenous administration, the active compounds are converted, if desired with the substances customary for this purpose, such as solubilizers, emulsifiers or other auxiliaries, into a solution, suspension or emulsion. Examples of suitable solvents are water, physiological saline or alcohols, for example ethanol, propanol or glycerol, as well as sugar solutions such as glucose or mannitol solutions, or else a mixture of the various solvents mentioned.

Examples of pharmaceutical formulations suitable for administration in the form of aerosols or sprays are solutions, suspensions or emulsions of the active substance of the formula I in a pharmaceutically acceptable solvent such as, in particular, ethanol or water, or a mixture of such solvents. The formulation can, if required, also contain other pharmaceutical auxiliaries such as surfactants, emulsifiers and stabilizers, as well as a propellant gas. A formulation of this type normally contains the active substance in a concentration of about 0.1 to 10, in particular of about 0.3 to 3, % by weight.

The dosage of the active substance of the formula I which is to be administered, and the frequency of administration, depend on the strength of action and duration of action of the compound used, and, additionally, on the nature and severity of the disease which is to be treated, as well as on the sex, age, weight and individual response of the mammal which is to be treated. On average, the recommended daily dose of a compound of the formula I for a patient weighing about 75 kg is at least 0.1 mg, preferably at least 1 mg, up to a maximum of 100 mg, preferably up to a maximum of 10 mg. In this connection, several, for example up to 4, single doses a day may be necessary for acute episodes of the disease, for example for attacks of asthma or of renal colic, whereas one dose may also suffice for prophylaxis.

In this connection, the compounds I can be administered alone or in combination with other compounds, for example when used for obstructive respiratory tract disorders with $\beta_2$-agonists such as salbutamol, or with theophylline or with disodium cromoglycate.

When used for disorders of the efferent urinary passages, examples of partners in the combination are those having antibacterial or analgesic activity.

The compounds of the formula I compiled in the table which follows are particularly well suited:

1) 2,2-dimethyl-3,4-dihydro-7-methoxy-6-(p-chlorophenyl-sulfonyl)-trans-4-(2-oxo-1-pyrrolidinyl)-2H-benzo[b]-pyran-3-ol,
2) 2,2-dimethyl-3,4-dihydro-6-(p-chlorophenylsulfonyl)-trans-4-(2-oxo-1-piperidinyl)-2H-benzo[b]pyran-3-ol,
3) 2,2-dimethyl-3,4-dihydro-6-(p-nitrophenylsulfonyl)-trans-4-(2-oxo-1-pyrrolidinyl)-2H-benzo[b]pyran-3-ol,
4) 2,2-dimethyl-3,4-dihydro-6-(p-cyanophenylsulfonyl)-trans-4-(2-oxo-1-pyrrolidinyl)-2H-benzo[b]pyran-3-ol,
5) 2,2-dimethyl-3,4-dihydro-6-(p-methoxyphenylsulfonyl)-trans-4-(2-oxo-1-pyrrolidinyl)-2H-benzo[b]pyran-3-ol,
6) 2,2-dimethyl-3,4-dihydro-6-(p-trifluoromethylphenylsulfonyl)-trans-4-(2-oxo-1-pyrrolidinyl)-2H-benzo[b]pyran-3-ol,
7) 2,2-dimethyl-3,4-dihydro-6-(p-methylsulfonylphenylsulfonyl)-trans-4-(2-oxo-1-pyrrolidinyl)-2H-benzo[b]pyran-3-ol,
8) 2,2-dimethyl-3,4-dihydro-6-(p-acetylphenylsulfonyl)-trans-4-(2-oxo-1-pyrrolidinyl)-2H-benzo[b]pyran-3-ol,
9) 2,2-dimethyl-3,4-dihydro-7-methylamino-6-phenylsulfonyl-trans-4-(2-oxo-1-pyrrolidinyl)-2H-benzo[b]pyran-3-ol,
10) 2,2-dimethyl-3,4-dihydro-7-fluoro-6-phenylsulfonyl-trans-4-(2-oxo-1-pyrrolidinyl)-2H-benzo[b]pyran-3-ol,
11) 2,2-diethyl-3,4-dihydro-7-fluoro-6-phenylsulfonyl-trans-4-(2-oxo-1-pyrrolidinyl)-2H-benzo[b]pyran-3-ol,
12) 2,2-dimethyl-7-chloro-3,4-dihydro-6-phenylsulfonyl-trans-4-(2-oxo-1-pyrrolidinyl)-2H-benzo[b]pyran-3-ol,
13) 2,2-dimethyl-3,4-dihydro-6-(4-chloro-3-methylphenylsulfonyl)-trans-4-(2-oxo-1-pyrrolidinyl)-2H-benzo[b]pyran-3-ol,
14) 2,2-dimethyl-3,4-dihydro-6-(4-chlorophenylsulfonyl)-trans-4-(5-oxo-3-thiazolidinyl)-2H-benzo[b]pyran-3-ol,
15) 2,2-dimethyl-3,4-dihydro-trans-4-(4-methyl-2-oxo-1-piperazinyl)-6-phenylsulfonyl-2H-benzo[b]pyran-3-ol,
16) 2,2-dimethyl-3,4-dihydro-6-phenylsulfonyl-trans-4-(2-oxo-1-morpholinyl)-2H-benzo[b]pyran-3-ol,
17) 2,2-dimethyl-3,4-dihydro-6-phenylsulfonyl-trans-4-(5-oxo-3-oxazolinyl)-2H-benzo[b]pyran-3-ol,
18) 3,4-dihydro-2,2-dimethyl-6-(p-fluorophenylsulfonyl)-trans-4-(2-oxo-1-pyrrolidinyl)-2H-benzo[b]pyran-3-ol,
19) 3,4-dihydro-2,2-dimethyl-6-(o-fluorophenylsulfonyl)-trans-4-(2-oxo-1-pyrrolidinyl)-2H-benzo[b]pyran-3-ol,
20) 3,4-dihydro-2,2-dimethyl-6-(3-pyridylsulfonyl)-trans-4-(2-oxo-1-pyrrolidinyl)-2H-benzo[b]pyran-3-ol,
21) 3,4-dihydro-2,2-dimethyl-6-(2-pyrimidinylsulfonyl)-trans-4-(2-oxo-1-pyrrolidinyl)-2H-benzo[b]pyran-3-ol,
22) 3,4-dihydro-2,2-dimethyl-6-(2-furylsulfonyl)-trans-4-(2-oxo-1-pyrrolidinyl)-2H-benzo[b]pyran-3-ol.

EXAMPLE 1

3,4-Dihydro-2,2-dimethyl-7-methoxy-6-(p-tolylsulfonyl)-trans-4-(2-oxo-1-pyrrolidinyl)-2H-benzo[b]pyran-3-ol 4,3 g (0.0097 mole) of 3-bromo-3,4-dihydro-2,2-dimethyl-7-methoxy-6-(p-tolylsulfonyl)-2H-benzo[b]pyran-4-ol are dissolved in 28 ml of dimethyl sulfoxide, and 3.5 ml of 2-pyrrolidinone (0.0465 mole) and 0.78 g of sodium hydride (80% suspension in oil) (0.0325 mole) are added, and the mixture is stirred at 40° C. for 3 hours. It is left to stand overnight and then poured onto ice-water and filtered with suction. The precipitate is recrystallized from isopropanol. White crystals of melting point: 263°–65° C.

PREPARATION OF THE STARTING COMPOUND

3-Bromo-3,4-dihydro-2,2-dimethyl-7-methoxy-6-(p-tolylsulfonyl)-2H-benzo[b]pyran-4-ol is obtained from 2,2-dimethyl-7-methoxy-6-(p-tolylsulfonyl)-2H-chromene and N-bromosuccinimide in a 9:1 mixture of dimethyl sulfoxide and $H_2O$. Melting point: 200°–201° C.

2,2-Dimethyl-7-methoxy-6-(p-tolylsulfonyl)-2H-chromene is obtained from 2,2-dimethyl-7-methoxy-6-(p-tolylsulfonyl)chroman-4-ol with phosphorus oxychloride/pyridine in benzene. Melting point: 132°–33° C.

2,2-Dimethyl-7-methoxy-6-(p-tolylsulfonyl)chroman-4-ol is obtained from 2,2-dimethyl-7-methoxy-6-(p-tolylsulfonyl)chroman-4-one with $NaBH_4$ in ethanol. Melting point: 196°–97° C.

2,2-Dimethyl-7-methoxy-6-(p-tolylsulfonyl)chroman-4-one is obtained from 2,2-dimethyl-7-methoxychroman-4-one and p-toluenesulfonyl chloride in the presence of aluminum chloride in methylene chloride. Melting point: 221°–23° C.

EXAMPLE 2

3,4-Dihydro-2,2-dimethyl-7-methoxy-6-(p-tolylsulfonyl)-trans-4-(2-oxo-1-piperidinyl)-2H-benzo[b]pyran-3-ol 5 g (0.011 mole) of 3-bromo-3,4-dihydro-2,2-dimethyl-7-methoxy-6-(p-tolylsulfonyl)-2H-benzo[b]pyran-4-ol are dissolved in 32 ml of dimethyl sulfoxide, and 4.9 g of valerolactam (0.0526 mole) and 0.8 g (0,033 mole) of NaH, 80% suspension in oil, are added, and the mixture is stirred at 40° C. for 5 hours. It is poured into ice-water and filtered with suction. The residue is extracted by boiling several times with methanol.

White crystals of melting point: 261°–63° C.

EXAMPLE 3

3,4-Dihydro-2,2-dimethyl-7-methoxy-6-phenylsulfonyl-trans-4-(2-oxo-1-pyrrolidinyl)-2H-benzo[b]pyran-3-ol The compound is prepared in analogy to Example 1 from 3-bromo-3,4-dihydro-2,2-dimethyl-7-methoxy-6-Phenylsulfonyl-2H-benzo[b]pyran-4-ol.

White crystals of melting point: 227°-29° C.

Separation of the Antipodes, Example 3a 1,075 g (0.0025 mole) of (±)-3,4-dihydro-2,2-dimethyl-7-methoxy-6-phenylsulfonyl-trans-4-(2-oxo-1-pyrrolidinyl)--2H-benzo[b]pyran-3-ol are dissolved in 5 ml of 1,2-dichlorobenzene, and 0.9 g of S(—)-1-phenylethyl isocyanate is added, and the mixture is stirred at 140° C. for about 12 h. The complete mixture is subsequently chromatographed on silica gel with the solvent system toluene/ethyl acetate 1:1. The diastereomeric carbamate which migrates slower can be enriched and obtained pure by crystallization from toluene (melting point 243°-245° C.). Hydrolysis with NaOH in EtOH at 80° C. results in (+)-3,4-dihydro-2,2-dimethyl-7-methoxy-6-phenylsulfonyl-trans-4-(2-oxo-1-pyrrolidinyl)-2H-benzo[b]pyran-3-ol of melting point: 209°-211° C. and $[\alpha]^D = +109°$ (c=0.28; CHCl$_3$)

Preparation of the Starting Material

3-Bromo-3,4-dihydro-2,2-dimethyl-7-methoxy-6-phenylsulfonyl-2H-benzo[b]pyran-4-ol is obtained from 2,2-dimethyl-7-methoxy-6-phenylsulfonyl-2H-chromene and N-bromosuccinimide in a 9:1 mixture of dimethyl sulfoxide and H$_2$O. Melting point: 202°-203° C.

2,2-Dimethyl-7-methoxy-6-phenylsulfonyl-2H-chromene is obtained from 2,2-dimethyl-4-hydroxy-7-methoxy-6-phenylsulfonylchromene with pyridine/phosphorus oxychloride in benzene. Melting point: 140°-41° C.

2,2-Dimethyl-4-hydroxy-7-methoxy-6-phenylsulfonylchroman is obtained from 2,2-dimethyl-7-methoxy-6-phenylsulfonylchroman-4-one with sodium borohydride in methanol.

Melting point: 146°-147° C.

2,2-Dimethyl-7-methoxy-6-phenylsulfonylchroman-4-one is obtained from phenylsulfonyl chloride, 2,2-dimethyl-7-methoxychroman-4-one and aluminum chloride in methylene chloride.

Melting point: 223°-25° C.

EXAMPLE 4

3,4-Dihydro-2,2-dimethyl-6-(4-methylphenylsulfonyl)-trans-4-(2-oxo-1-pyrrolidinyl)-2H-benzo[b]pyran-3-ol 0.75 g (0.025 mole) of 80% NaH is introduced into 8.2 g (0.02 mole) of 3-bromo-3,4-dihydro-2,2-dimethyl-6-(4-methylphenylsulfonyl)-2H-benzo[b]pyran-4-ol in 30 ml of dimethyl sulfoxide. After stirring at 20° for one hour, a further 0.75 g (0.025 mole) of 80% NaH and 1.9 ml (0,025 mole) of 2-pyrrolidone are added, and the mixture is stirred at 40° for 45 minutes and at 20° for 6 hours. It is introduced into ice-water and then the precipitate is filtered off with suction, dried and recrystallized from methanol several times.

Crystals of melting point: 242°-243° C.

Preparation of the Starting Material

3-Bromo-3,4-dihydro-2,2-dimethyl-6-(4-methylphenylsulfonyl)-2H-benzo[b]pyran-4-ol 14.2 g (0.08 mole) of freshly recrystallized N-bromosuccinimide are introduced into 12.6 g (0.04 mole) of 2,2-dimethyl-6-(4-methylphenylsulfonyl)chromene in a solution composed of 70 ml of dimethyl sulfoxide and 1.4 ml of water while cooling (isopropanol/dry ice) at about 15° C. The temperature rises transiently to 27°. It is cooled to 20° C. and, after stirring for one hour, introduced into ice/ethyl acetate. The ethyl acetate phase is washed several times with water and dried over Na$_2$SO$_4$. The bromohydrin derivative crystallizes on concentration. Crystals of melting point: 141°-142° C.

EXAMPLE 5

3,4-Dihydro-2,2-dimethyl-6-phenylsulfonyl-trans-4-(2-oxo-1-pyrrolidinyl)-2H-benzo[b]pyran-3-ol A solution of 6.3 g (0.02 mole) of 3,4-dihydro-2,2-dimethyl-3,4-epoxy-6-phenylsulfonyl-2H-benzo[b]pyran in 20 ml of DMSO is added dropwise, at 20°, to a suspension of 0.6 g (0.02 mole) of 80% NaH in 10 ml of DMSO. Then 2.3 ml (0.03 mole) of 2-pyrrolidinone are added, and the mixture is stirred at 45° for one hour. After it has stood at 20° overnight it is introduced into ice-water. The precipitate is filtered off with suction, washed to neutrality, dried and chromatographed on silica gel with methylene chloride/methanol 19:1. 30 ml fractions are collected. Fractions 12–22 are concentrated, and the residue is recrystallized from acetonitrile.

Melting point: 201°-202°

Preparation of the Starting Material 3,4-Dihydro-2,2-dimethyl-3,4-epoxy-6-phenylsulfonyl-2H-benzo[b]pyran is obtained from 3-bromo-3,4-dihydro-2,2-dimethyl-6-phenylsulfonyl-2H-benzo[b]pyran-4-ol with NaH in DMSO.

Melting point: 103°-105°

3-Bromo-3,4-dihydro-2,2-dimethyl-6-phenylsulfonyl-2H-benzo[b]pyran-4-ol is obtained from 2,2-dimethyl-6-phenylsulfonyl-2H-chromene and N-bromosuccinimide in 9:1 mixture of dimethyl sulfoxide and H$_2$O.

Melting point: 126°

2,2-Dimethyl-6-phenylsulfonyl-2H-chromene, with melting point 70°-71°, was prepared by known methods from 4-phenylsulfonylphenyl 1,1-dimethylpropargyl ether. This ether is obtained, likewise in a known manner, from 4-phenylsulfonylphenol and 3-methyl-3-chlorobutyne.

(+)-3,4-Dihydro-2,2-dimethyl-6-phenylsulfonyl-4-(2-oxo-1-pyrrolidinyl)-2H-benzo[b]pyran-3-ol (Example 5a)

(±)-3,4-Dihydro-2,2-dimethyl-6-phenylsulfonyl-4-(2-oxo-1-pyrrolidinyl)-2H-benzo[b]pyran-3-ol is esterified with (—)-menthoxyacetyl chloride by standard methods. The diastereomeric esters are separated on a silica gel column with methylene chloride/ethyl acetate (9:1) and hydrolyzed by stirring at 20° with alcoholic sodium ethylate solution. After dilution with cold water, the precipitate is filtered off with suction and washed to neutrality and triturated with ether. (+)-3,4-Dihydro-2,2-dimethyl-6-phenylsulfonyl-4-(2-oxo-1-pyrrolidinyl)-2H-benzo[b]pyran-3-ol Melting point: 122°-123° $[\alpha]_D = +39.5°$ (c=1, ethanol)

EXAMPLE 6

6-(4-Chlorophenylsulfonyl)-3,4-dihydro-2,2-dimethyl-7-methoxy-trans-4-(2-oxo-1-pyrrolidinyl)-2H-benzo[b]-Pyran-3-ol The compound is prepared in analogy to Example 1 from 3-bromo-6-(4-chlorophenylsulfonyl)-3,4-dihydro-2,2-dimethyl-7-methoxy-2H-benzo[b]pyran-4-ol.

White crystals with melting point: 260°-262° C.

Preparation of the Starting Compounds

In analogy to Example 1:
3-Bromo-6-(4-chlorophenylsulfonyl)-3,4-dihydro-2,2-dimethyl-7-methoxy-2H-benzo[b]pyran-4-ol with melting point: 175°–177° C.
6-(4-Chlorophenylsulfonyl)-2,2-dimethyl-7-methoxychromene with melting point: 142°–143° C.

EXAMPLE 7

6-(4-Bromophenylsulfonyl)-3,4-dihydro-2,2-dimethyl-7-methoxy-trans-4-(2-oxo-1-pyrrolidinyl)-2H-benzo[b]-pyran-3-ol In analogy to Example 1 from 3-bromo-6-(4-bromophenylsulfonyl)-3,4-dihydro-2,2-dimethyl-7-methoxy-2H-benzo[b]pyran-4-ol.
White crystals of melting point: 281°–282° C.

EXAMPLE 8

3,4-Dihydro-2,2-dimethyl-7-methoxy-6-(4-methoxyphenylsulfonyl)-trans-4-(2-oxo-1-pyrrolidinyl)-2H-benzo[b]pyran-3-ol The compound is prepared in analogy to Example 1 from 3-bromo-3,4-dihydro-2,2-dimethyl-7-methoxy-6-(4-methoxyphenylsulfonyl)-2H-benzo[b]pyran-4-ol and has a melting point of 286°–287° C.

EXAMPLE 9

3,4-Dihydro-2,2-dimethyl-7-methoxy-6-(2-thienylsulfonyl)-trans-4-(2-oxo-1-pyrrolidinyl)-2H-benzo[b]pyran-3-ol In analogy to Example 1 from 3-bromo-3,4-dihydro-2,2-dimethyl-7-methoxy-6-(2-thienylsulfonyl)-2H-benzo[b]pyran-4-ol, melting point: 135°–136° C.

EXAMPLE 10

3,4-Dihydro-2,2-dimethyl-7-ethoxy-6-phenylsulfonyl-trans-4-(2-oxo-1-pyrrolidinyl)-2H-benzo[b]pyran-3-ol In analogy to Example 1 from 3-bromo-3,4-dihydro-2,2-dimethyl-7-ethoxy-6-phenylsulfonyl-2H-benzo[b]pyran-4-ol, melting point: 197°–198° C.

EXAMPLE 11

3,4-Dihydro-2,2-dimethyl-7-methoxy-6-phenylsulfonyl-trans-4-(2-oxo-1-piperidinyl)-2H-benzo[b]pyran-3-ol In analogy to Example 2 from 3-bromo-3,4-dihydro-2,2-dimethyl-7-methoxy-6-phenylsulfonyl-2H-benzo[b]-pyran-4ol. White crystals of melting point: 157°–158° C.

EXAMPLE 12

6-(4-Cyanophenylsulfonyl)-3,4-dihydro-2,2-dimethyl-trans-4-(2-oxo-1-pyrrolidinyl)-2H-benzo[b]pyran-3-ol In analogy to Example 1 from 3-bromo-6-(4-cyanophenylsulfonyl)-3,4-dihydro-2,2-dimethyl-2H-benzo[b]-pyran-4-ol.
White crystals of melting point: 234°–235° C.

Preparation of the Starting Material
3-Bromo-6-(4-cyanophenylsulfonyl)-3,4-dihydro-2,2-dimethyl-2H-benzo[b]pyran-4-ol is obtained as described in Example 3 from 6-(4-cyanophenylsulfonyl)-2,2-dimethyl-3-chromene.
Melting point: 157°–158° C.

EXAMPLE 13

3,4-Dihydro-2,2-dimethyl-6-(2-methoxyphenylsulfonyl)-trans-4-(2-oxo-1-pyrrolidinyl)-2H-benzo[b]pyran-3-ol In analogy to Example 1 from 3-bromo-3,4-dihydro-2,2-dimethyl-6-(2-methoxyphenylsulfonyl)-2H-benzo[b]pyran-4-ol. White crystals of melting point: 196°–198° C.

EXAMPLE 14

3,4-Dihydro-2,2-dimethyl-6-(2-methylphenylsulfonyl)-trans-4-(2-oxo-1-pyrrolidinyl)-2H-benzo[b]pyran-3-ol In analogy to Example 1. White crystals of melting point: 214°–216° C.

EXAMPLE 15

3,4-Dihydro-2,2-dimethyl-6-(2-chlorophenylsulfonyl)-trans-4-(2-oxo-1-pyrrolidinyl)-2H-benzo[b]pyran-3-ol In analogy to Example 1. White crystals of melting point: 85°–87° C.

EXAMPLE 16

Preparation of 3,4-dihydro-2,2-dimethyl-6-phenylsulfonyl-trans-4-(2-oxo-1-pyrrolidinyl)-2H-benzo[b]pyran-3-ol (compound of Example 5 by process variant c)

A solution of 3-bromo-3,4-dihydro-2,2-dimethyl-6-phenylsulfonyl-2H-benzo[b]pyran-4-ol in ethanol is shaken under a pressure of 8 bar of $NH_3$ at 50° in an autoclave for 8 hours. The mixture is cooled and then evaporated to dryness and recrystallized from ethyl acetate. 4-Amino-3,4-dihydro-2,2-dimethyl-6-phenylsulfonyl-2H-benzo[b]pyran-3-ol of melting point: 160°–163°C. is obtained and is immediately subjected to acylation with 4-chlorobutyryl chloride. For this purpose, the substance is dissolved together with the acid chloride in $CH_2Cl_2$ and stirred in a two-phase mixture with 2N sodium hydroxide solution at room temperature for 24 hours. The usual working up results in 4-(4-chlorobutyrylamino)-3,4-di-hydro-2,2-dimethyl-6-phenylsulfonyl-2H-benzo[b]pyran-4-ol of melting point 155°–157° C. Cyclization to give the title compound is carried out by dissolving the substance in tetrahydrofuran, addition of a stoichiometric amount of 80% NaH suspension in oil and stirring the mixture at room temperature for 24 hours. The final product is identical to the product obtained by process b). Melting point: 200°–201° C. If 4-amino-3,4-dihydro-2,2-dimethyl-6-phenylsulfonyl-2H-benzo[b]pyran-3-ol is subjected to racemate resolution, it is possible to obtain from its (+) enantiomer the pure (+) enantiomer from Example 5a with the data indicated there.

EXAMPLE 17

3,4-Dihydro-2,2-dimethyl-6-phenylsulfoxy-trans-4-(2-oxo-1-pyrrolidinyl)-2H-benzo[b]pyran-3-ol In analogy to Example 1. Melting point: 211°–212° C.
Pharmacological data
a) Effect on respiratory tract disorders Effect on histamine-induced bronchoconstriction in guinea-pigs
Method
White guinea-pigs of both sexes and weighing between 450 and 550 g were anesthetized with 60 mg/kg pentobarbital i.p. After tracheotomy, they were ventilated with a Starling pump (from Braun, Melsungen). The tidal volume was selected for generous ventilation of the lungs. The ventilation pressure was adjusted to 80 mm H₂O with the aid of a water column (Rosenthal and Dervinis). The breathing rate was 30 breaths/min. An excess of available respiratory air can pass through a bypass in the inhalation tube to a washbottle which is designed as a water pressure-relief valve. When air is blown by the Starling pump through the inhalation tube into the lungs they are inflated until the pressure in the system has reached the value set by the height of the water column (80 mm H₂O). The continuing inflow of air flows through the pressure-relief valve into the washbottle. This excess air which escapes into the bottle after the set pressure has been exceeded is measured with the aid of a piston recorder and is taken as a measure of the change in the airway resistance. Measurement was carried out in a manner slightly modified from the original Konzett-Rossler method, in that the piston recorder was replaced by a Fleisch dynamic pressure tube (type 0000). The difference in pressure which occurred was detected with Statham PM 97 TC differential pressure transducer. A Hellige multichannel pen recorder was used to record the measurements.

The test substances are administered as aerosol with the aid of an ultrasonic atomizer (Monaghan M 650). The atomizer chamber is interpolated in the inhalation tube of the ventilation pump and allows the animals to inhale the aerosol for 1 min. The volume to be atomized is 0.02 ml/min.

Used for atomization is a physiological saline solution to which the substance to be tested is added in the form of a solution in propanediol.

It is ensured, in a control experiment, that the solvent propanediol/physiological saline solution has no action itself.

Bronchoconstriction is induced by doses of histamine dihydrochloride (6–12 μg/kg i.v.). Injection is through a catheter introduced into the jugular vein. The dose is selected so that a respiratory "overflow" of 60% of the offered tidal volume occurs during the histamine-induced bronchoconstriction. The histamine doses are given at intervals of 5 minutes. After at least 3 well-reproduced bronchoconstrictions, the test substances are administered as aerosol for 1 min and, after an action time of 2 min, the bronchoconstriction is induced anew and repeated at intervals of 5 minutes.

The degree of inhibition of the histamine-induced broncho-constriction after pretreatment with the test substance is regarded as a measure of the bronchodilator activity and is reported as % change from the control.

All results are subjected to linear regression, and the $ID_{50}$ is determined.

Results

| % inhibition of histamine-induced bronchoconstriction | | | |
|---|---|---|---|
| Compound | Dose | n | % inhibition |
| Example 5a | 1 μg/kg | 6 | 14 ± 4 |
| (+)-3,4-dihydro-2,2-dimethyl-6-phenyl-sulfonyl-trans-4-(2-oxo-1-pyrrolidinyl)-2H-benzo[b]pyran-3-ol | 3 μg/kg | 6 | 35 ± 4 |
| | 10 μg/kg | 6 | 77 ± 7 |

$ID_{50}$: 4.39 μg/kg b) Efferent urinary passages Effect on the KCl-induced rhythmic contractions of the guinea-pig ureter in vitro Method Male guinea-pigs were sacrificed by a blow to the back of the neck and exsanguination from the carotids. The two ureters were immediately removed, avoiding the region near the renal pelvis because of the pacemaker activity present there. Pieces 2 cm long were first freed of connective tissue in a Petri dish containing Tyrode solution and then suspended in a 25 ml organ bath (from Rhema Labortechnik, Hofheim), in each case with a tension of 4.9 mN (=0.5 p). The organ bath contained Tyrode solution of the following composition (mmol/l): NaCl 137, KCl 2.68, MgSO₄ 1.05, CaCl₂ 1.8, NaH₂PO₄ 0.41, NaHCO₃ 11.9, glucose 5.55, which was maintained at 37° C. and through which carbogen (95% O₂, 5% CO₂) was bubbled.

The contractions were measured isometrically using Gould/Statham UC2 pickups. After an equilibration time of at least 15 minutes, KCl was added to the organ bath to reach a concentration of $4 \times 10^{-2}$ mol/l. The agonist was left in the bath for 2 minutes, during which phasic contractions occurred without bringing about any noteworthy increase in the basic line tension.

Rinsing was then carried out for 1 minute, the rhythmic contractions ceasing immediately. After a second run with addition of agonist and the rinsing procedure, the test substance (benzopyran derivative) was added to the organ bath (in the form of a solution in 0.1 ml of ethanol; the final concentration was $10^{-7}$ mol/l in all cases) and was allowed to act for one minute before KCl was added. The subsequent rinsing procedure was followed by two final additions of agonist/rinsing procedures.

The following parameters were determined in each of the two-minute periods during which KCl acted: 1. mean force of contraction, 2. frequency of contractions and 3. product of mean force and frequency of contractions.

The criteria for exclusion were mean forces of contraction below 4 mN or frequencies of below 2/min in more than one of the four periods in which only the agonist KCl was present in the bath. Evaluation was of the percentage inhibition with the test substance compared with the mean value from the two initial runs.

Besides the arithmetic mean (x), the standard error of the mean (SEM) was calculated.

Results

| Compound | Mean force of contraction k (%) | Frequency v % | k · v % | n |
|---|---|---|---|---|
| 3,4-Dihydro-2,2-dimethyl-6-(2-chlorophenylsulfonyl)-trans-4-(2-oxo-1-pyrrolidinyl)-2H-benzo[b]pyran-3-ol Example 15 | 68 ± 11 | 67 ± 14 | 85 ± 7 | 4 | n = number of ureters
Reference:
R. Schiantarelli and W. Murmann, Arzneimittel-Forschung/Drug Research 30, 1102-1109 (1980)

We claim:

1. A method of treating a smooth muscle disorder of the respiratory system, which comprises administering to a host in need of such treatment an effective amount of a compound of the formula I;

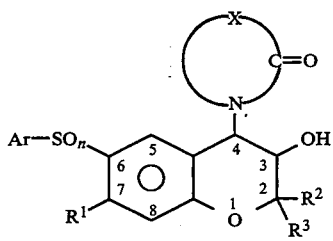

wherein:
R$^1$ represents H, OH, (C$_1$–C$_2$)-alkoxy, (C$_1$–C$_2$)-alkyl or NR$^4$R$^5$, where R$^4$ and R$^5$ are identical or different and represent H, (C$_1$–C$_2$)-alkyl or (C$_1$–C$_3$)-alkyl-carbonyl;

R$^2$ and R$^3$ are identical or different and represent alkyl having 1–4 carbon atoms;

Ar represents an aromatic system which is unsubstituted or substituted by 1 to 3 identical or different radicals selected from (C$_1$–C$_2$)-alkyl, (C$_1$–C$_2$)-alkoxy, halogen, trifluoromethyl, CN, NO$_2$, SO$_m$—(C$_1$–C$_2$)-alkyl wherein m represents the integers 1 or 2, and CO—(C$_1$–C$_2$)-alkyl radicals;

n represents the integers 1 or 2; and x represents a (CH$_2$)$_r$ chain which may be interrupted by O, S or a NR$^6$ group, wherein R$^6$ represents H or (C$_1$–C$_4$)-alkyl, and r represents the integers 2, 3, 4, or 5.

2. The method of treating a smooth muscle disorder of the respiratory system according to claim 1, wherein:
R$^1$ to R$^3$, Ar, and n have the same meanings as claimed in claim 1; and
x represents a (CH$_2$)$_r$ chain wherein r represents the integers 3 or 4.

3. The method of treating a smooth muscle disorder of the respiratory system according to claim 1, wherein:
R$^1$ to R$^3$ have the same meanings as claimed in claim 1;
Ar represents phenyl which is unsubstituted or substituted as claimed in claim 1; and
X represents a (CH$_2$)$_r$ chain wherein r represents the integers 3 or 4.

4. The method of treating a smooth muscle disorder of the respiratory system according to claim 1, wherein:
R$^1$ represents hydrogen;
R$^2$ and R$^3$ represent (C$_1$–C$_2$)-alkyl;
Ar represents phenyl which is unsubstituted or substituted once by (C$_1$–C$_2$)-alkyl, (C$_1$–C$_2$)-alkoxy or halogen;
n represents the integer 2; and
x represents a (CH$_2$)$_r$ chain wherein r represents the integers 3 or 4.

5. The method of treating a smooth muscle disorder of the respiratory system according to claim 1, wherein:
R$^1$ represents hydrogen;
R$^2$ and R$^3$ represent (C$_1$–C$_2$)-alkyl;
Ar represents phenyl;
n represents the integer 2; and
x represents (CH$_2$)$_3$.

6. A method of treating a smooth muscle disorder of the respiratory system, which comprises administering to a host in need of such treatment an effective amount of 3,4-dihydro-2,2-dimethyl-6-phenylsulfonyl-trans-4-(2-oxo-1-pyrrolidinyl)-2H-benzo[b]pyran-3ol.

7. The method of treating a smooth muscle disorder of the respiratory system according to claim 1, wherein the smooth muscle disorder is asthma.

* * * * *